US011279279B2

United States Patent
Tamrakar et al.

(10) Patent No.: US 11,279,279 B2
(45) Date of Patent: Mar. 22, 2022

(54) DRIVER MONITORING AND RESPONSE SYSTEM

(71) Applicants: SRI International, Menlo Park, CA (US); Toyota Motor Corporation, Toyota (JP)

(72) Inventors: Amir Tamrakar, New Brunswick, NJ (US); Girish Acharya, Redwood City, CA (US); Makoto Okabe, Kariya (JP); John James Byrnes, Poway, CA (US)

(73) Assignees: SRI International, Menlo Park, CA (US); Toyota Motor Corporation, Aichi (JP)

( * ) Notice: Subject to any disclaimer, the term of this patent is extended or adjusted under 35 U.S.C. 154(b) by 165 days.

(21) Appl. No.: 16/472,760

(22) PCT Filed: Dec. 19, 2017

(86) PCT No.: PCT/US2017/067369
§ 371 (c)(1),
(2) Date: Jun. 21, 2019

(87) PCT Pub. No.: WO2018/118958
PCT Pub. Date: Jun. 28, 2018

(65) Prior Publication Data
US 2021/0129748 A1  May 6, 2021

Related U.S. Application Data

(60) Provisional application No. 62/438,422, filed on Dec. 22, 2016, provisional application No. 62/438,419, filed on Dec. 22, 2016.

(51) Int. Cl.
*B60Q 1/00* (2006.01)
*B60Q 9/00* (2006.01)
(Continued)

(52) U.S. Cl.
CPC ............. *B60Q 9/00* (2013.01); *A61B 5/0077* (2013.01); *A61B 5/1103* (2013.01);
(Continued)

(58) Field of Classification Search
CPC ......... B60Q 9/00; A61B 5/163; A61B 5/0077; A61B 5/1103; A61B 5/1114;
(Continued)

(56) References Cited

U.S. PATENT DOCUMENTS

2014/0159887 A1* 6/2014 Piasecki ............... B60Q 1/00
340/438
2014/0212853 A1   7/2014 Divakaran et al.
(Continued)

OTHER PUBLICATIONS

International Search Report and Written Opinion, PCT/US2017/037369, ISA:US, dated Dec. 27, 2018, 9 pp.

*Primary Examiner* — Naomi J Small
(74) *Attorney, Agent, or Firm* — Rutan & Tucker, LLP

(57) ABSTRACT

An evaluation engine has two or more modules to assist a driver of a vehicle. A driver drowsiness module analyzes monitored features of the driver to recognize two or more levels of drowsiness of the driver of the vehicle. The driver drowsiness module evaluates drowsiness of the driver based on observed body language and facial analysis of the driver. The driver drowsiness module is configured to analyze live multi-modal sensor inputs from sensors against at least one of i) a trained artificial intelligence model and ii) a rules based model while the driver is driving the vehicle to produce an output comprising a driver drowsiness-level estimation. A driver assistance module provides one or more positive assistance mechanisms to the driver to return the driver to be at or above the designated level of drowsiness.

20 Claims, 10 Drawing Sheets

(51) Int. Cl.
*A61B 5/16* (2006.01)
*A61B 5/00* (2006.01)
*A61B 5/11* (2006.01)
*A61B 5/18* (2006.01)
*G06F 3/16* (2006.01)
*G06K 9/00* (2022.01)

(52) U.S. Cl.
CPC ........... *A61B 5/1114* (2013.01); *A61B 5/1116* (2013.01); *A61B 5/1128* (2013.01); *A61B 5/163* (2017.08); *A61B 5/18* (2013.01); *A61B 5/7267* (2013.01); *A61B 5/741* (2013.01); *A61B 5/749* (2013.01); *G06F 3/167* (2013.01); *G06K 9/00845* (2013.01); *A61B 2560/0443* (2013.01)

(58) Field of Classification Search
CPC ....... A61B 5/1116; A61B 5/1128; A61B 5/18; A61B 5/7267; A61B 5/741; A61B 5/749; A61B 2560/0443; G06F 3/167; G06K 9/00845
USPC .......................................................... 340/439
See application file for complete search history.

(56) References Cited

U.S. PATENT DOCUMENTS

| | | |
|---|---|---|
| 2014/0212854 A1 | 7/2014 | Divakaran et al. |
| 2014/0347475 A1 | 11/2014 | Divakaran et al. |
| 2015/0296135 A1* | 10/2015 | Wacquant .......... G06K 9/00261 348/207.11 |
| 2015/0314681 A1* | 11/2015 | Riley, Sr. ................ G08B 21/06 340/576 |
| 2016/0026253 A1* | 1/2016 | Bradski ................ H04N 13/167 345/8 |
| 2016/0071024 A1 | 3/2016 | Amer et al. |
| 2016/0117725 A1* | 4/2016 | Capel ................. G06Q 30/0266 705/14.52 |
| 2016/0154882 A1 | 6/2016 | Cheng et al. |
| 2016/0170996 A1* | 6/2016 | Frank ................ G06F 16/24578 707/748 |
| 2016/0328967 A1* | 11/2016 | Haag ................. G08G 1/096775 |
| 2017/0160813 A1 | 6/2017 | Divakaran et al. |
| 2018/0239975 A1 | 8/2018 | Tamrakar et al. |

* cited by examiner

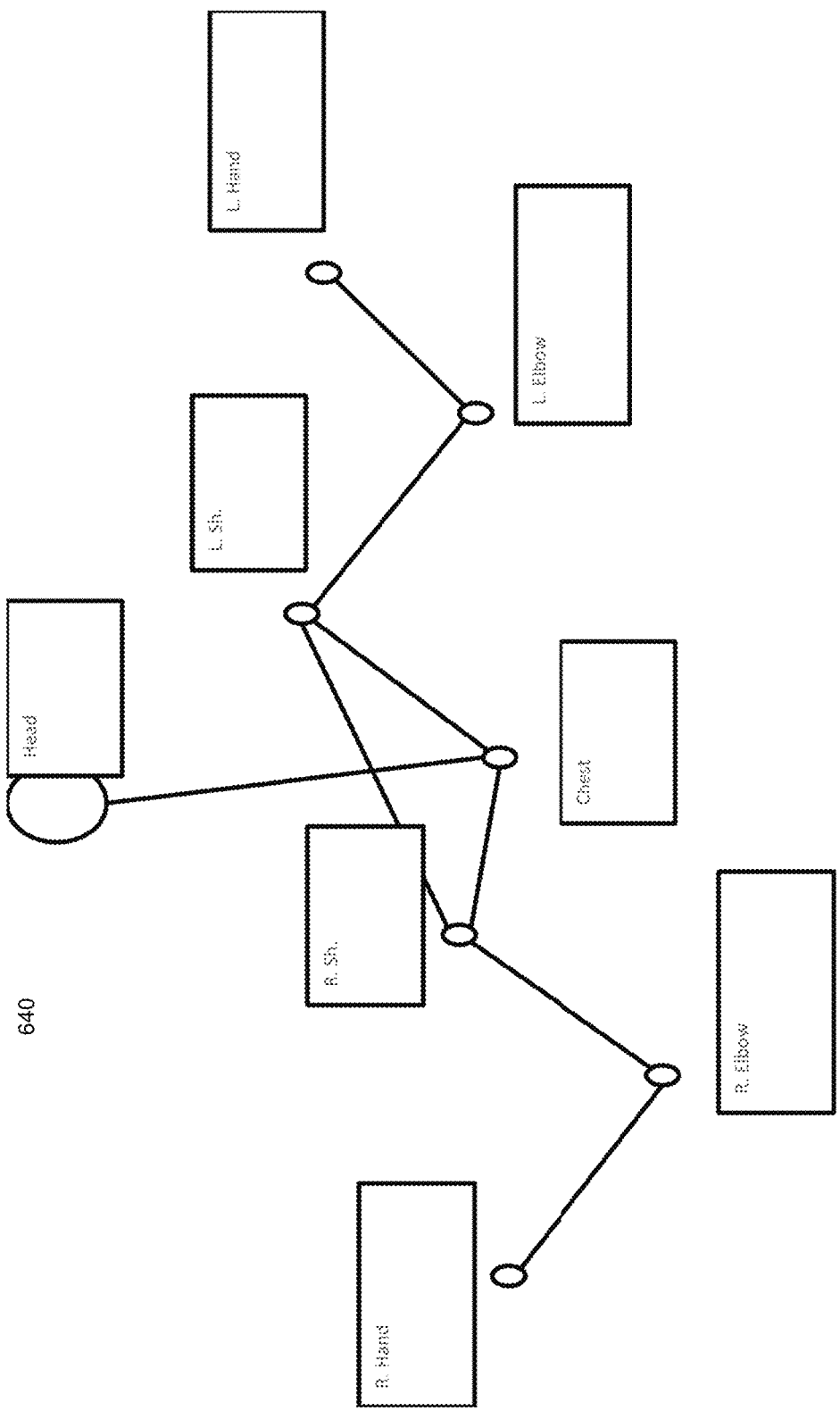
Fig. 6  The skeletal representation for upper body torso tracking

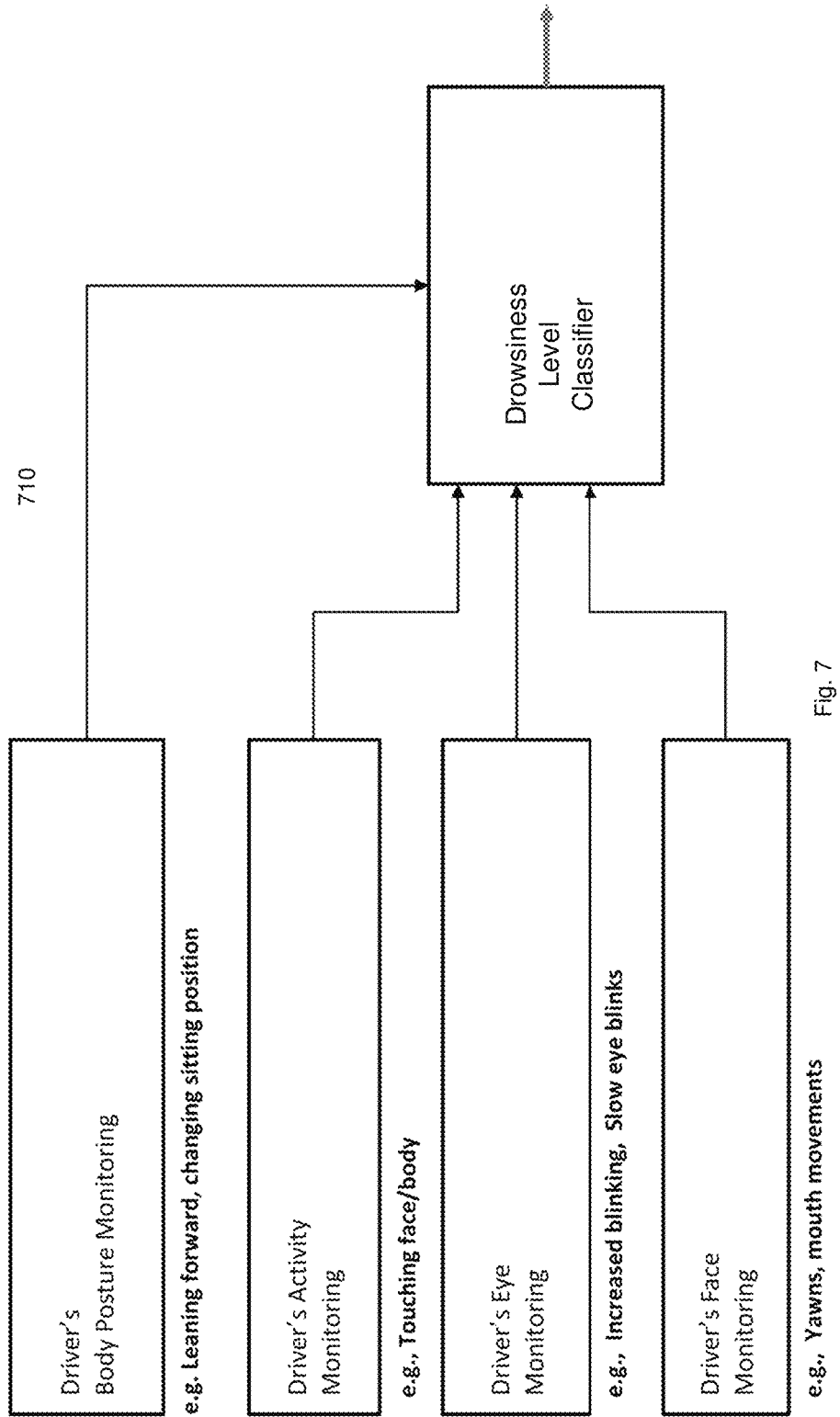

```
                              ( Cont. )
                                  |
```

| |
|---|
| Analyzing live multi-modal sensor inputs from the sensors against at least one of i) a trained machine-learning model and ii) a rules based model or iii) both while the driver is driving the vehicle to produce an output comprising a driver drowsiness-level estimation, where the driver drowsiness module using the trained machine-learning model and/or the rules based model is configured to utilize fewer computing cycles to classify a current level of drowsiness of the driver of the vehicle than the driver drowsiness module not using the trained machine-learning model and/or the rules based model.     812 |
| Using both i) a generic drowsy-level machine learning model trained on analyzing the two or more features of the driver to recognize the two or more levels of drowsiness of the driver of the vehicle as well as ii) a user-personalized drowsy-level machine-learning model trained on any specifics of this driver to recognize the two or more levels of drowsiness of the driver, where the combination of the generic drowsy-level machine learning model trained on analyzing the two or more features of the driver and the user-personalized drowsy-level machine-learning model trained on any specifics of this driver causes the evaluation engine to more rapidly recognize the level of drowsiness of the driver than by using the generic drowsy-level machine learning model by itself.     814 |
| Using a driver assistance module to attempt to maintain the driver i) in a non-drowsiness level, ii) at or below a first level of drowsiness of the driver, and iii) any combination of both, based on an output from the driver drowsiness module; and, when the driver is not at least at or below the first level of drowsiness of the driver, then provideone or more positive assistance mechanisms back to the driver to attempt to change the driver's level to the level of i) where the driver is the non-drowsiness level, ii) where the driver's level of drowsiness is lowered to a lower level of drowsiness, and iii) any combination of both.     816 |
| Using a driver assistance module to provide a positive assistance mechanism of engaging the driver with a personalized spoken summary through speakers of the vehicle, based on the driver's current level of drowsiness as determined by the driver drowsiness module, that is i) variable in decibel level, ii) selection of what kind of content of a document that the driver assistance module believes to be of interest to the driver, or iii) both variable in decibel level as well as what kind of content of the document that the system believes to be of interest to the driver.     818 |

Fig. 8B           ( End )

DRIVER MONITORING AND RESPONSE SYSTEM

CROSS-REFERENCE

This application is a 35 U.S.C. § 371 U.S. National Stage of International Patent Application No. PCT/US2017/067369, titled "A Driver Monitoring and Response System" having an International Filing Date of Dec. 19, 2017 which claims the benefit of and priority under 35 USC 119 to U.S. provisional patent application Ser. 62/438,422, Titled "Automated estimation of drowsiness level of a driver of a vehicle," filed Dec. 22, 2016, and U.S. provisional patent application Ser. 62/438,419, and Titled "Alertness assistance for a driver of a vehicle" filed Dec. 22, 2016, both of which are hereby incorporated in, in their entirety.

NOTICE OF COPYRIGHT

A portion of the disclosure of this patent application contains material that is subject to copyright protection. The copyright owner has no objection to the facsimile reproduction by anyone of the software engine and its modules, as it appears in the United States Patent & Trademark Office's patent file or records, but otherwise reserves all copyright rights whatsoever.

FIELD

Embodiments of the design provided herein generally relate to a driver monitoring and response system.

BACKGROUND

Over worked and/or tired drivers on the road cause many problems on the road. Having a vehicle configured with intelligence and sensors to detect and respond to a driver being in a drowsy level will help improve the safety on the road.

SUMMARY

Provided herein are various methods, apparatuses, and systems for a driver monitoring and response system.

In an embodiment, an evaluation engine has two or more modules to assist a driver of a vehicle. A driver drowsiness module analyzes monitored features of the driver to recognize two or more levels of drowsiness of the driver of the vehicle. A facial analysis module performs at least one of i) face tracking and ii) eye blink tracking on the driver of the vehicle to assist in detecting the levels of drowsiness of the driver of the vehicle. An output analysis of the facial analysis module is supplied to the driver drowsiness module. A sensor interface is located among the two or more modules (including the facial analysis module and the driver drowsiness module) and one or more sensors located in the vehicle. The one or more sensors located in the vehicle include i) one or more cameras, and ii) a motion sensing device, to monitor the driver of the vehicle. The driver drowsiness module is configured to utilize the output of the facial analysis module to evaluate drowsiness of the driver based on observed body language and facial analysis of the driver, to detect and classify two or more levels of drowsiness of the driver of the vehicle. The driver drowsiness module is configured to analyze live multi-modal sensor inputs from the sensors against at least one of i) a trained artificial intelligence model, ii) a rules based model, or iii) both while the vehicle is started to produce an output comprising a driver drowsiness-level estimation. The driver drowsiness module using the trained artificial intelligence model and/or the rules based model is configured to utilize fewer computing cycles to classify a current level of drowsiness of the driver of the vehicle than the driver drowsiness module not using the trained artificial intelligence model and/or the rules based model. A driver assistance module attempts to maintain at or above a designated level of drowsiness of the driver based on an output from the driver drowsiness module. When the driver is not at or above the designated level of drowsiness of the driver, then the driver assistance module provides one or more positive assistance mechanisms back to the driver to return the driver to be at or above the designated level of drowsiness.

These and other features of the design provided herein can be better understood with reference to the drawings, description, and claims, all of which form the disclosure of this patent application.

DRAWINGS

The drawings refer to some embodiments of the design provided herein in which:

FIG. 6 illustrates a block diagram of the driver activity module utilizing a skeletal model of a driver.

FIG. 7 illustrates a block diagram of the driver drowsiness module.

FIGS. 8A-8B illustrate flow diagrams of an embodiment of an evaluation engine.

Figure 1:
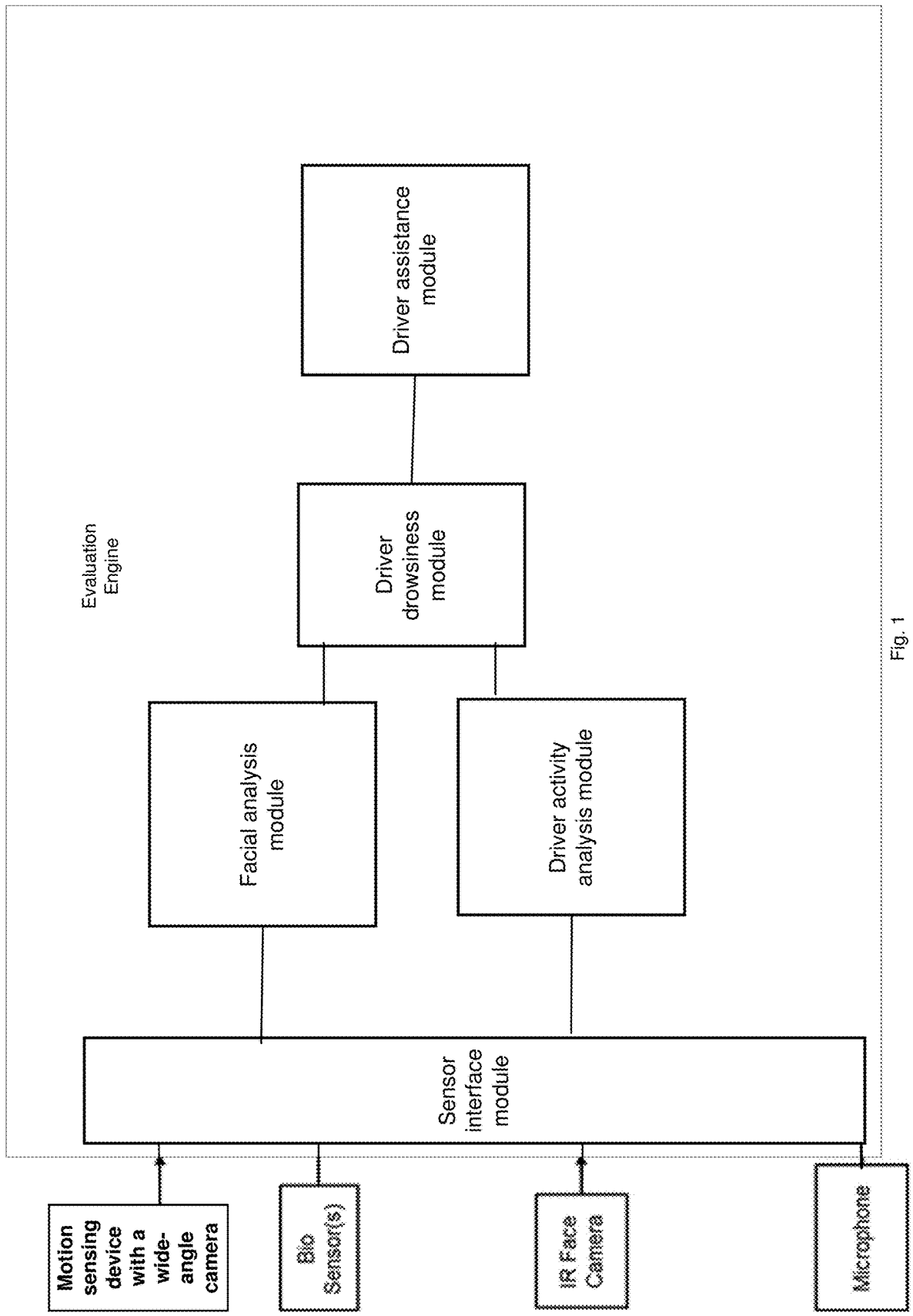
FIG. 1 illustrates a block diagram of an embodiment of an evaluation engine having two or more modules to assist a driver of the vehicle.

While the design is subject to various modifications, equivalents, and alternative forms, specific embodiments thereof have been shown by way of example in the drawings and will now be described in detail. It should be understood that the design is not limited to the particular embodiments disclosed, but—on the contrary—the intention is to cover all modifications, equivalents, and alternative forms using the specific embodiments.

DESCRIPTION

In the following description, numerous specific details are set forth, such as examples of specific data signals, named components, number of frames of images captured, etc., in order to provide a thorough understanding of the present design. It will be apparent, however, to one of ordinary skill in the art that the present design can be practiced without these specific details. In other instances, well known components or methods have not been described in detail but rather in a block diagram in order to avoid unnecessarily obscuring the present design. Further, specific numeric references such as the first computing device, can be made. However, the specific numeric reference should not be interpreted as a literal sequential order but rather interpreted that the first computing device is different than a second computing device. Thus, the specific details set forth are merely exemplary. The specific details can be varied from and still be contemplated to be within the spirit and scope of the present design. The term "coupled" is defined as meaning connected either directly to the component or indirectly to the component through another component.

In general, one or more embodiments of an evaluation engine system are discussed. In an embodiment, an evaluation engine has two or more modules to assist a driver of a vehicle. A driver drowsiness module analyzes monitored features of the driver to recognize two or more levels of drowsiness of the driver of the vehicle. The driver drowsiness module evaluates drowsiness of the driver based on observed body language and facial analysis of the driver. The driver drowsiness module is configured to analyze live multi-modal sensor inputs from sensors against at least one of i) a trained artificial intelligence model and ii) a rules based model while the driver is driving the vehicle to produce an output comprising a driver drowsiness-level estimation. A driver assistance module provides one or more positive assistance mechanisms to the driver to return the driver to be at or above the designated level of drowsiness.

FIG. 1 illustrates a block diagram of an embodiment of an evaluation engine having two or more modules to assist a driver of the vehicle. The evaluation engine 100 may include various modules including a facial analysis module, a biological signal estimation module, a driver drowsiness module, and a driver of assistance module. The evaluation engine 100 may have additional modules and sub modules including a driver's face tracking module, a driver's gaze module, a driver's eye blinking tracking module, a driver's facial expression monitoring module, a body language based down in motion recognition module, a facial expression based emotion recognition module, a speech based emotion recognition module, and a multi-modal fusion of the emotion estimation module. The evaluation engine 100 may receive input from a number of different sensors, such as, a motion sensing device with a wide angle camera, an infrared camera narrowly focused on the face of the driver, a microphone, various biosensors attached to the driver, such as, smart watch that sends its Bluetooth signals to the vehicle's information system, and other similar sensors on the driver or installed in the vehicle.

The evaluation engine 100, can be an artificial intelligence and/or rule based engine that has rules or training to assist a driver of a vehicle. The evaluation engine 100 uses its two or more modules to enhance driver safety and facilitate a safe and relaxed driving experience by performing either or both i) a drowsiness estimations or ii) a drowsiness estimation.

The driver drowsiness module is configured to analyze monitored features of the driver to recognize two or more levels of drowsiness of the driver of the vehicle. The driver drowsiness module monitors to make an automated estimation of drowsiness level of a driver of a vehicle. The driver drowsiness module integrates a multi-modal analysis including two or more features including: facial expression analysis, gaze behavior analysis, ocular activity analysis, blinking profiles, eye closure patterns, body language analysis including smoothness and rapidness of movements/postures/activities, and potentially speech sentiment analysis. The driver drowsiness module may include a generic drowsy-level artificial-intelligence model and a user-personalized drowsy-level artificial intelligence model.

The facial analysis module that is configured to track and perform at least i) face tracking ii) eye blink tracking, iii) an eye lid open/close ratio, iv) a duration of eye closure or eyes forced open events, v) facial expression analysis, and vi) driver gaze tracking on the driver of the vehicle to assist in detecting the levels of drowsiness of the driver of the vehicle. The output analysis of the facial analysis module is supplied to the driver drowsiness module. The facial analysis module may have an ocular activity analysis module that is configured to cooperate with an infra-red light source to track a direction of a head of the driver relative a steering wheel of the vehicle and an angle of a gaze of the eyes of the driver of the vehicle. The ocular activity analysis module can implement a glint-based tracking mechanism that tracks corneal glints from the infra-red light source.

The sensor interface interfaces between the two or more modules, including the facial analysis module, the driver drowsiness module, etc., and the one or more sensors located in the vehicle. The one or more sensors located in the vehicle include i) one or more cameras, ii) a motion sensing device coupled with a speech user interface (e.g. Kinect sensor), to monitor the driver of the vehicle. In an embodiment, the sensor interface receives a multi-modal sensor input from at least three sensors of i) the motion sensing device coupled with the speech user interface that includes a close talking microphone, ii) a hi-resolution InfraRed camera that produces at least 300 dpi (dots per inch) images that is coupled to one or more InfraRed light sources in the vehicle that are positioned to narrowly focus on a face of the driver, and iii) a wide-angle lens, three-dimensional depth, camera positioned to capture a view of the driver's head and upper body. Note, the wide-angle lens three-dimensional depth camera is optionally discrete from the motion sensing device.

The driver activity analysis module cooperates with the sensor interface to receive an input from the wide-angle depth camera in the vehicle in order to perform a head pose tracking relative to a body of the driver. The driver activity analysis module uses an algorithm to three dimensionally determine a head position of the driver relative to the images input provided by the wide-angle depth camera.

The driver drowsiness module utilizes i) deep learning from a driver activity module and ii) the output of the facial analysis module to evaluate attentiveness/drowsiness of the driver, based on observed body language, facial analysis, content and/or tone of voice of the driver, and other forms of expression of the driver, in order to detect and classify two or more levels of drowsiness of the driver of the vehicle. The driver assistance module is configured to attempt to maintain at or above a designated level of drowsiness of the driver based on an output from the driver drowsiness module. When the driver is not at or above this level of drowsiness of the driver, then the driver assistance module provides one or more positive assistance mechanisms back to the driver to return the driver to the designated level of drowsiness. The driver assistance module is configured to attempt to anticipate the needs of the driver in real time and attempt to keep the driver in a non-drowsy state or at least at or above a marginally drowsy level.

Figure 2:
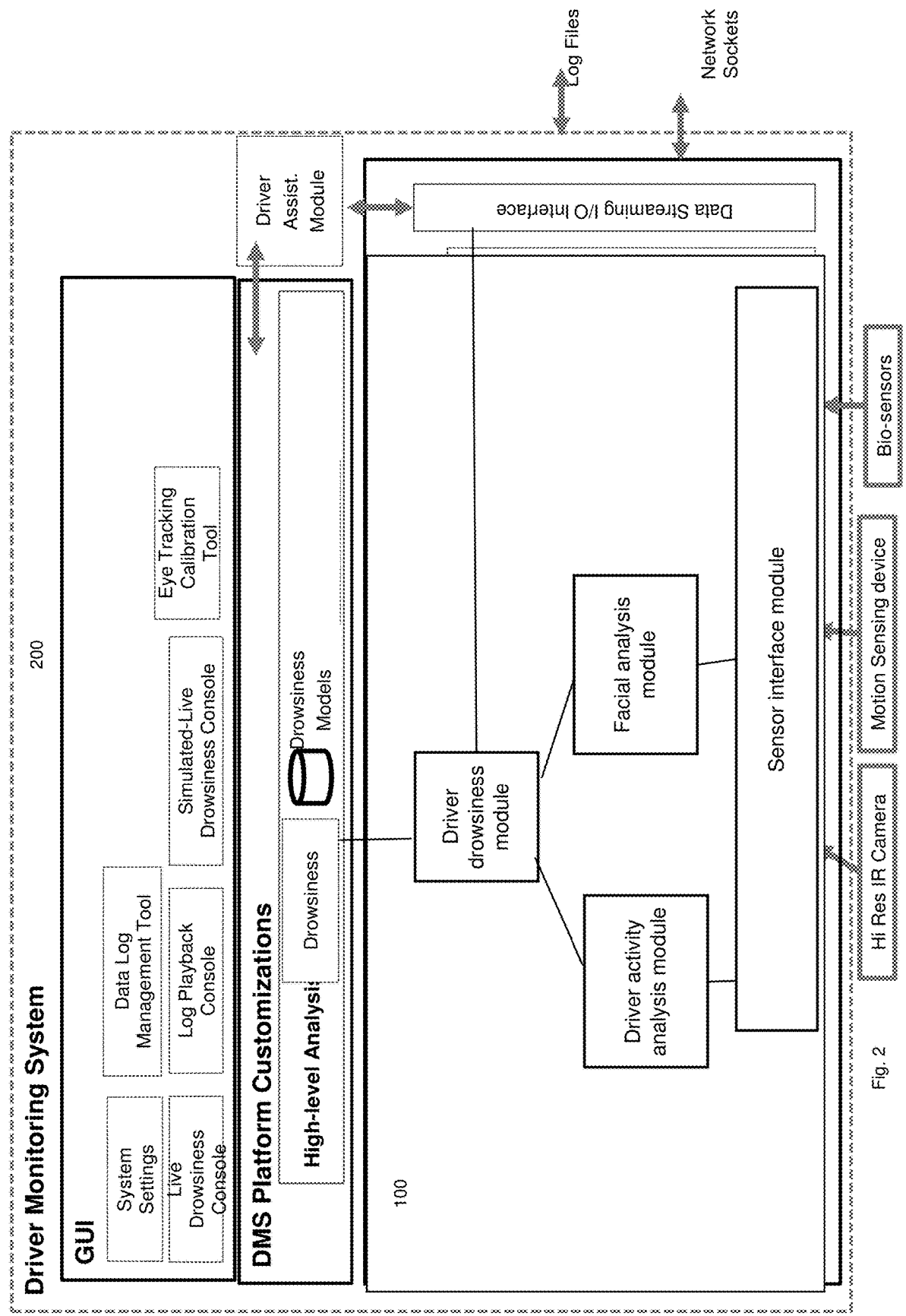
FIG. 2 illustrates a block diagram of an embodiment of an evaluation engine to monitor and alert a driver of the vehicle.

FIG. 2 illustrates a block diagram of another embodiment of an evaluation engine to monitor and alert a driver of the vehicle. The evaluation engine 200 may have a driver monitoring system graphical user interface, a driver monitoring system customization's platform, a driver monitoring platform, and a driver's assistance module.

The evaluation engine 200, such as an artificial intelligence and/or rule based engine, has the two or more modules to assist a driver of a vehicle. A module, such as the driver drowsiness module, may use i) a driver drowsiness machine learning model trained on detecting drowsiness indicators, ii) a rules-based model with similar rules coded in and iii) a combination of both.

The driver drowsiness module is configured to integrate a multi-modal analysis from i) the sensors and ii) one or more driver-drowsiness machine-learning models trained on detecting drowsiness indicators of the driver or a rules-based model with similar rules coded in that indicate drowsiness of the driver. The driver drowsiness module integrates the multi-modal analysis on two or more features including: i) facial expression analysis for the face tracking, ii) driver's gaze behavior analysis for the eye movement, iii) eye blinking profiles and analysis for the eye blink tracking, iv) eye closure pattern analysis, and v) body language analysis including smoothness and rapidness of movements/postures/activities, and vi) potentially speech sentiment analysis including speech tones and words. In an embodiment, the engine may utilize all of these features in its analysis.

In an embodiment, the driver drowsiness module includes both a generic drowsy-level machine learning model trained on analyzing monitored features of the driver to recognize the two or more levels of drowsiness of the driver of the vehicle as well as trained on user-personalized drowsy-level machine-learning model. To do this, the system first builds a driver-specific drowsiness model using a machine learning subsystem. The system receives estimations of driver drowsiness level that are specific to this particular driver. The combination of the generic drowsy-level machine learning model trained on analyzing the two or more features of the driver and the user-personalized drowsy-level machine-learning model trained on any specifics of this driver causes the evaluation engine to more rapidly recognize the level of drowsiness of the driver than by using the generic drowsy-level machine learning model by itself. The system uses multi-modal sensor inputs (training data), ground truth correlations, and a drowsiness level classification scheme that has at least two or more different levels of drowsiness of the driver, to train the model using machine learning algorithms. In an embodiment, various machine learning artificial intelligence models using Deep Neural Networks are utilized in the different modules for tracking, analysis, and recognition. The driver drowsiness module may then analyze live multi-modal sensor inputs from the sensors against the models to generate appropriate mechanisms in real time.

The system may use multi-modal behavior cues detected by the vision and other sensing systems that the driver is in a specific level of drowsiness. Computer vision algorithms are used to extract driver behavior cues from the training data. The training data may be annotated with the behavior cues that are detected by the computer vision algorithms. Examples of driver behavior cues include eye movements, such as blinking (and blink rate), yawning, touching face, rubbing eyes, leaning forward, leaning back, moving arms or hands, etc.

An example drowsiness level classification scheme is shown in Table 1 below. As shown, each drowsiness level is defined by a combination of multiple different driver behavioral cues.

Drowsiness Level Chart

TABLE 1

Drowsiness Level Chart

| Category | Driver Behavioral Cues | Level |
|---|---|---|
| Non Drowsy | Quick and frequent eye movements<br>Stable cycle of eye blink<br>Quick and active body movements | 0 |
| Levels of Drowsiness | | |
| Marginally Drowsy | Opening mouth including yawns<br>Slow eye movement | 1 |
| Moderately Drowsy | Slow and frequent eye blinks<br>Mouth movements<br>Changing the sitting position<br>Touching face/neck | 2 |
| Significantly Drowsy | Intentional eye blinks and head shakes<br>Unnecessary body movement such as shoulders moving up-and-down<br>Frequent yawns and intentional deep breaths<br>Slow eye blinks and eye movements | 3 |
| Exceedingly Drowsy | Eyes closing or closed<br>Body leaning forward and neck outstretched<br>Head leaning behind against the head rest | 4 |
| Sleeping | Eyes fully closed | 5 |

Note, the driver assistance module is configured such that when the driver is not at or above a set point level of drowsiness of the driver, then the driver assistance module is configured to provide one or more positive assistance mechanisms back to the driver to attempt to change the driver's level to a level i) where the driver is not in one of the levels of drowsiness (e.g. Non Drowsy), ii) where the driver's level of drowsiness is lowered to a lower level of drowsiness, and any combination of both. For example, the driver's level of drowsiness is lowered to a lower level of drowsiness when the positive assistance mechanisms lowers the driver's level of drowsiness from Sleeping level 5 to Marginally Drowsy level 1. In this example, Marginally Drowsy level 1 is at or above the set point level of drowsiness of the driver.

Next, the driver activity analysis module is configured to cooperate with the sensor interface to receive input from a number of sensors. For example, the driver activity analysis module may cooperate with the sensor interface to use a time-of-flight camera (ToF camera) in the motion sensing device to track a driver's upper-body. The camera could also be a RGB camera. The driver activity analysis module is configured to track the driver's upper-body posture and movement using the motion sensor's data stream.

Figure 3:
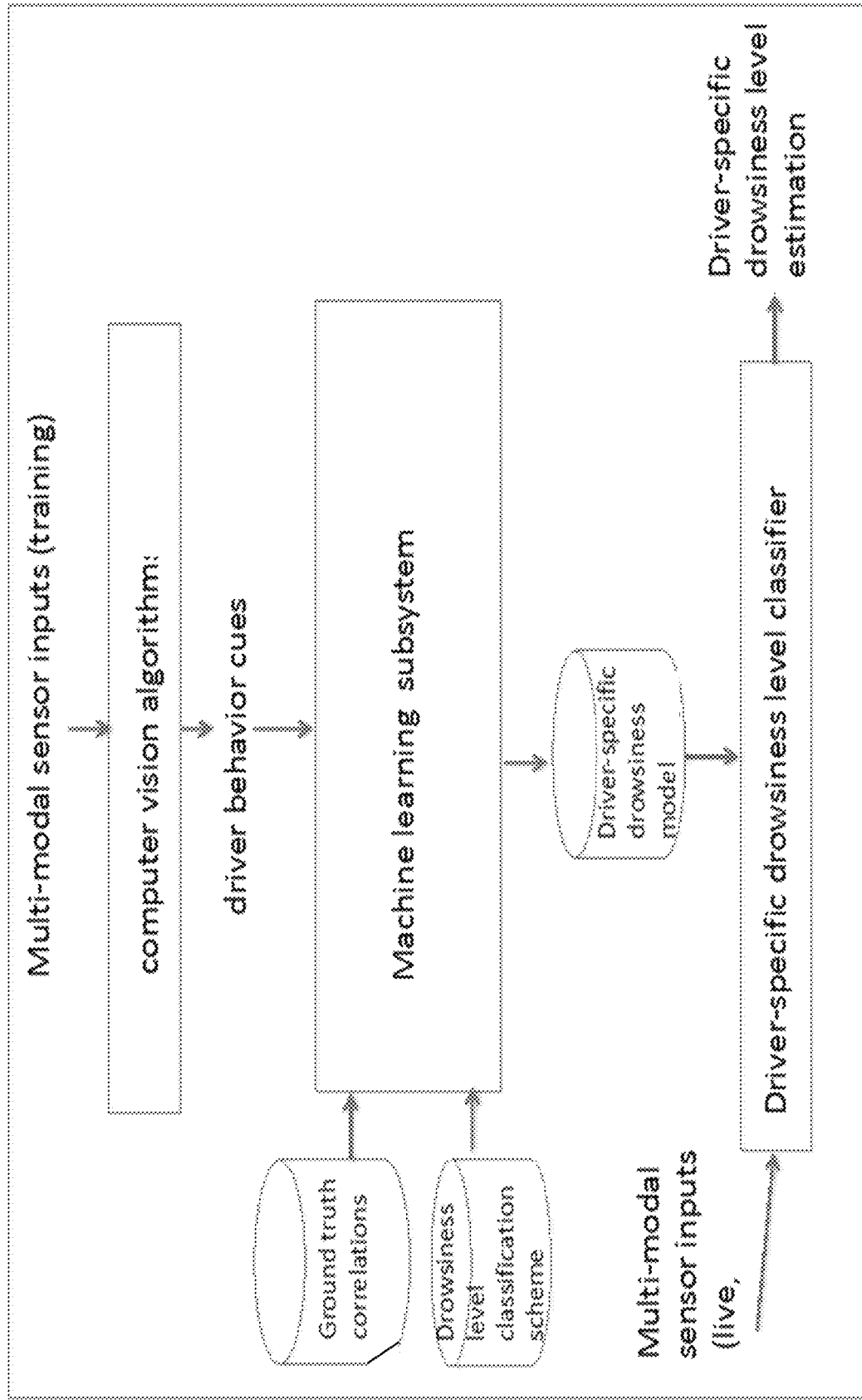
FIG. 3 illustrates a block diagram of a driver drowsiness module that can estimate the drowsiness level of the driver of the vehicle.

FIG. 3 illustrates a block diagram of a driver drowsiness module that can estimate the drowsiness level of the driver of the vehicle. The driver drowsiness module 310 can receive and analyze multimodal sensor inputs. The driver drowsiness model can utilize computer vision algorithms to analyze the video and still image inputs from the various cameras. The driver drowsiness model may include a module that is trained on driver behavior issues and analyzes for those cues on the level of drowsiness of the driver. The driver drowsiness module 310 may include a machine learning subsystem that utilizes ground truth correlations from a database and/or library of correlations as well as drowsiness level classification schemes from a database and/or a library. The driver drowsiness module 310 may be trained to be driver specific and have a database behaviors specifically trained to the behaviors of that specific driver. The driver drowsiness module 310 made then generate a driver specific drowsiness level classifier and make a driver specific drowsiness level estimation.

In an embodiment, the one or more driver-drowsiness machine-learning models trained on detecting drowsiness indicators of the driver include both i) a generic drowsy-level machine learning model trained on analyzing the two or more features of the driver to recognize the two or more levels of drowsiness of the driver of the vehicle as well as ii) a user-personalized drowsy-level machine-learning model trained on any specifics of this driver to recognize the two or more levels of drowsiness of the driver.

In an embodiment, the one or more driver-drowsiness machine-learning models utilize ground truth correlations and deep learning machine learning algorithms to train the models. The one or more driver-drowsiness machine-learning models use a drowsiness level classification scheme that has at least three or more different levels of drowsiness of the driver. Also, once the one or more driver-drowsiness machine-learning models are trained, they are used to analyze live multi-modal sensor inputs from the sensors while the driver is driving the vehicle to produce an output including a level of drowsiness estimation specific to that driver. The ground truth correlations associate driver behavior cues, or combinations of different driver behavior cues, with different levels of the drowsiness level classification scheme. Thus, the model indicates the relative importance of different behavioral cues to the above drowsiness levels, for the specific user. Note, different behavioral cues may be more or less important indicators of drowsiness, for different drivers.

Once the model is trained, it can be used by a classifier to analyze live multi-modal sensor inputs while the driver is driving the vehicle. The classifier produces output comprising driver-specific drowsiness level estimations. The system may output the drowsiness level estimations as annotations to at least some of the input data. The output may further include indications of changes in the driver's drowsiness level over time. The predictive estimations of the driver's drowsiness level can be input to, for example, a personal assistant system or a driver safety system.

Figure 4:
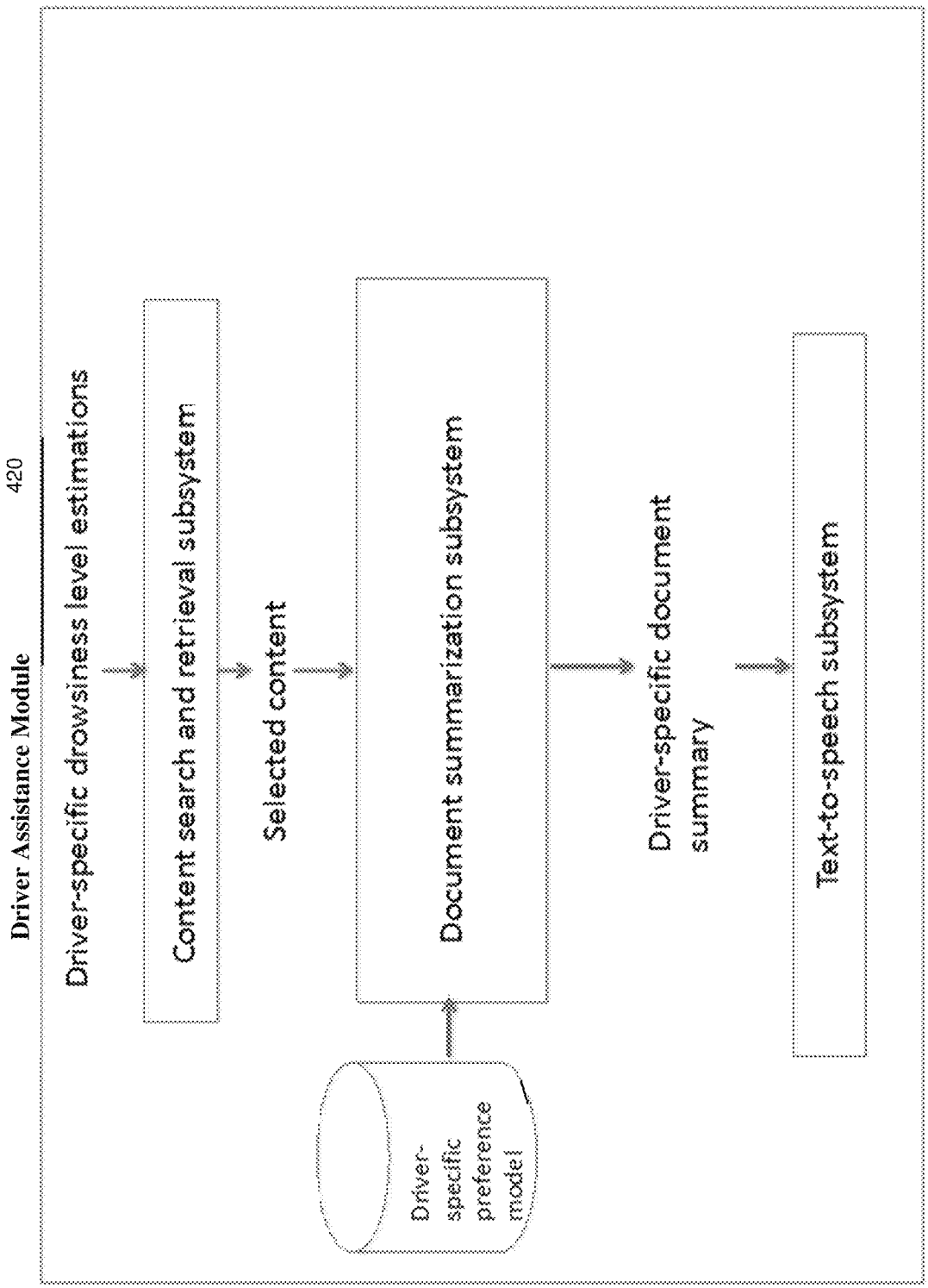
FIG. 4 illustrates a block diagram of a driver's assistance module.

FIG. 4 illustrates a block diagram of a driver's assistance module. The driver's assistance module 420 may include a module for driver specific drowsiness and level estimations and a content search and retrieval module. The driver's assistance module 420 may utilize this to select content and perform a document summarization. The driver's assistance module 420 can reference a database of pre-existing document summarizations that are continually generated and updated by the document summarization module as well as may create a document summarization in real-time on, for example, a blog, an internet article, or twitter stream. The database of document summarizations may reference a driver specific reference model. The visual analysis module may perform facial recognition to automatically identify the identity of who is driving the vehicle. The document summarization module will then generate driver specific documents and send that to a text-to-speech module, which will then play through the speaker system of the vehicle. The driver's assistance module 420 will attempt to engage in a bi-directional conversation using the speakers and a microphone regarding the one or more document summaries with the driver in an attempt to bring the driver back to a non-drowsy state or at least a marginally drowsy level.

The driver assistance module 420 may provide one or more assistance mechanisms to engage the driver with, for example, a personalized spoken (audio) summary, based on the driver's current level of drowsiness as determined by the driver drowsiness module. The personalized spoken (audio) summary may be i) variable in decibel level, ii) selection of what kind of content of a document that the driver assistance module 420 believes to be of interest to the driver, or iii) both variable in decibel level as well as what kind of content of the document that the system believes to be of interest to the driver. The driver assistance module monitors and evaluates the level of drowsiness of the driver as the personalized spoken summary is occurring; and the material on what kind of content of the document is being presented, changes as the level of drowsiness of the driver changes.

The driver assistance module 420 may utilize a document summarization engine to produce an extractive summary of the content of the document. The driver-specific preference model extracts driver preferences from texts, browsing habits, and input solicited from the user. For example, to achieve free conversation, a summarization of WEB data from a Web document, like Wikipedia, could be extracted and then have summary of that content. The text-to-speech subsystem in the driver assistance module 420 is used to prepare the summarized content of the document to report to the driver through a speaker of the vehicle and then engage in a dialog via gathering the driver's responses with the microphone associated with the speech to text module.

The driver assistance module 420 initiates a search for content of possible interest using a content search and retrieval subsystem. Once the selected content is retrieved, the driver assistance module 420 prepares a personalized summary of the selected content, by using a document summarization subsystem and a driver-specific preference model.

The document summarization subsystem utilizes the document summarization engine to produce an extractive summary of the content. The driver-specific preference model may be developed using personal user modeling platforms, which may extract driver preferences from text (such as web pages, Twitter feeds and other social media content) using natural language processing techniques. A text-to-speech subsystem is used to prepare the summarized content for presentation to the driver through a speaker of the automobile. The text-to-speech subsystem may include a conversational personal assistant to engage in a dialog with the driver.

The driver-specific preference model tries to assist the alertness of that driver of a vehicle by choices for that specific driver. In addition, the evaluation engine receives estimations of driver drowsiness level that are also specific to the particular driver.

The conversational personal assistant is configured to adapt the interactive conversation between itself and the driver in real time based on the feedback from the user and the current level of drowsiness of the driver as indicated by the output from the driver activity tracking module. The driver assistance module provides one or more positive assistance mechanisms back to the driver to attempt to change the driver's level of drowsiness including the summary of content, the engaging in dialog, running the fan, air conditioner, changing the temp in the car, shaking the seat, changing the smells in the vehicle, etc.

The driver assistance module 420 may interface with a personal assistant system, which may engage the driver in a dialog to further tailor the retrieved content to the driver's interests, or to modulate the presentation of summarized content based on driver reactions detected by the multi-modal vision and sensing systems.

The driver assistance module 420 may conclude based on multi-modal behavior cues detected by the vision and sensing systems that the driver is reacting positively to the presented content summary, and as a result may continue reading additional details from the summarized document. On the other hand, if the driver assistance module 420 hypothesizes that the driver's interest in the summarized content is waning, or if the driver's level is detected as increasing in drowsiness level, the driver assistance module may change the topic or discontinue the presentation of summarized content.

The real-time driver monitoring by the driver assistance module 420 allows for assistance to be presented to the driver and then the assistance module 420 can make a real time assessment of what effect the assistance had on the level of drowsiness of the driver. Thus, whether additional or combinations of different types of assistance should further be presented to the driver to return the driver to at least the desired level of drowsiness such as non drowsy or marginally drowsy.

The driver may engage in a dialog with the evaluation engine and the driver can dismiss the evaluation engine for trying to launch an assistance. However, if the driver continues to progress more in level of severity of drowsiness, then the assistance module 420 can eliminate the driver's ability to dismiss the launching of an assistance.

Figure 5:
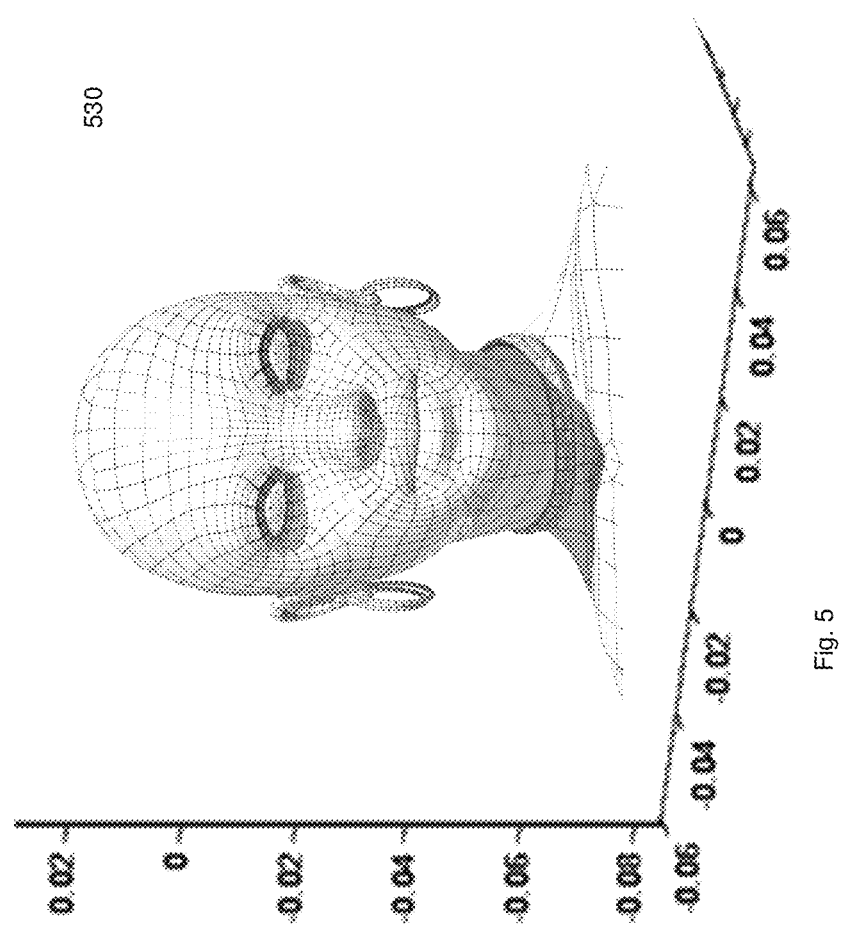
FIG. 5 shows an illustration of the facial analysis module performing facial analysis with a facial model on tasks such as face tracking of the driver, eye blink tracking of the driver, facial expression analysis of the driver, driver gaze tracking, eye closure pattern analysis of the driver, etc.

FIG. 5 shows an illustration of the facial analysis module performing facial analysis with a facial model on tasks such as face tracking of the driver, eye blink tracking of the driver, facial expression analysis of the driver, driver gaze tracking, eye closure pattern analysis of the driver, etc. Those features are analyzed in the facial model 530 to determine the drowsiness level of the driver. The facial analysis module is coded to perform a driver's face detection with landmarks tracking.

The facial analysis module uses the camera and algorithms to do robust facial landmark tracking (±50 degrees from center). The facial analysis module uses multiple facial landmarks, for example, 51 separate facial landmarks located on a typical human face. The more facial landmarks the camera and algorithm the camera capture and populate in the facial model 530, the more accurate the analysis. The facial analysis module may be customized to the features and activity patterns for that specific driver for improved accuracy.

The facial analysis module may have an Ocular Activity Analysis module that has a cooperating infra red light source to track a direction and angle of a gaze of the eyes of the driver. Thus, the Ocular Activity Analysis module may implement a glint-based driver's gaze tracking mechanism. The Ocular Activity Analysis module tracks a pair of corneal glints from the InfraRed Light Emitting Diodes and the pupil center (dark pupil). The Ocular Activity Analysis module is able to detect eye closure patterns incorporating race into its analysis. The Ocular Activity Analysis module is able to select the Infra-Red illuminator Light Emitting Diodes from a larger set to increase FOV (when glints fall outside the cornea) as well as be robust to large disruptive glares on glasses.

The Ocular Activity Analysis module can use head pose and iris tracking-to base the determination of where the driver is gazing. The Ocular Activity Analysis module uses head pose and iris tracking to determine gaze vectors and determine glance targets. The Ocular Activity Analysis module may know or determine the images in the frames captured by the camera relative to the vehicle cabin coordinates and/or known landmarks in the vehicle.

The facial analysis module may also perform facial expression monitoring. The facial analysis module may also perform driver's eyelid monitoring. The facial analysis module may normalize the head-pose to eyelid tracking. The facial analysis module is binarized to eye closure detection. The facial analysis module determines and tracks things such as i) eye blinking rates, ii) eye lid open/close ratio, and iii) eye closure duration events including micro-sleep event and eyes forcefully kept open. Note, eye blinking patterns, such as eye blinking rates and eye lid open/close ratio, as well as eye closure duration events may be stored in a memory for tracking purposes.

FIG. 6 illustrates a block diagram of the driver activity module utilizing a skeletal model of a driver. The skeletal model 640 represents the upper body and torso of the driver being tracked in the vehicle. The driver activity module tracks and analyzes the driver's activity including, for example, how fast and how many body parts are moving as well as how smooth or jerky the movement is. The driver activity module stores the driver's activity. The driver's activity module analyzes the movements and activity compared to the norms in the trained skeletal model 640 as well as changes over time. The driver activity module analyzes those features and sends its analysis out in order to determine the drowsiness level of the driver.

A model has been trained on a driver's activity and posture monitoring. The upper body and torso has been trained on. Some activities and postures indicative of drowsiness are as follows: changing seating position; head resting on hands; yawning; rubbing eyes; touching face; leaning back, arms stretched; and leaning forward.

The driver drowsiness module incorporates both body language signals and eye monitoring in its multimodal drowsiness level estimation and classification.

FIG. 7 illustrates a block diagram of the driver drowsiness module. The example driver drowsiness module 710 may have many sub blocks including, for example, a driver's body posturing monitoring block, a driver's activity monitoring block, a driver's eye monitoring block, and a driver's face monitoring block. All of these different blocks feed into the drowsiness level classifier module. The driver's body posture monitoring block may monitor things, for example, how the driver's body is leaning forward and/or changing seating position, how often and the posture of that seating position, etc. The driver's activity monitor module may track things, for example, like the driver touching their face and/or touching various parts of the body and how often they are touching their face in various parts of their body. The driver's eye monitoring module tracks eye movements, such as how often the driver's eyes are blinking, what rate the eye's are blinking, as well as a duration of whether the eyes are shut and/or how long those eyes are being forced open. The driver's face monitoring module tracks and analyzes things for example yawn and mouth movements of the driver. Again, the drowsiness level classifier receives this multimodal imports regarding the driver's drowsiness level and then applies various weighting algorithms to determine a level of drowsiness of the driver. Based on the level of the drowsiness of the driver, the driver assistant module will then determine what level of assistance the driver needs in order to get back to a proper level of non drowsiness. The drowsiness level classifier module may also determine that the driver is currently in a non drowsy level.

Figure 8A:
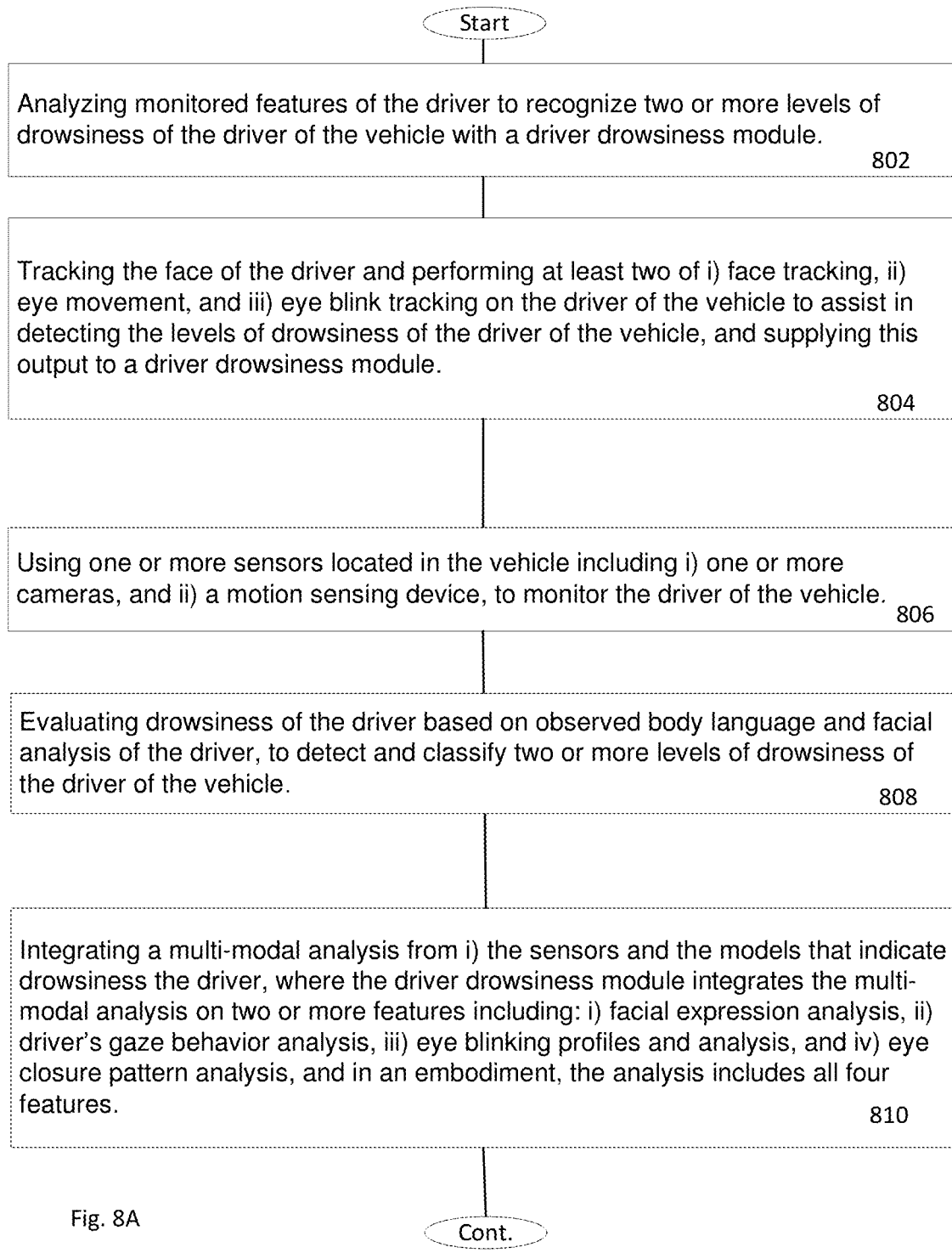

FIGS. 8A-8B illustrate flow diagrams of an embodiment of an evaluation engine. Note, the following steps may be performed in any order where logically possible. A method for an evaluation engine to assist a driver of a vehicle is discussed and performs the following operations.

In step 802, analyzing monitored features of the driver to recognize two or more levels of drowsiness of the driver of the vehicle with a driver drowsiness module.

In step 804, tracking the face of the driver and performing at least two of i) face tracking, ii) eye movement, and iii) eye blink tracking on the driver of the vehicle to assist in detecting the levels of drowsiness of the driver of the vehicle, and supplying this output to a driver drowsiness module.

In step 806, using one or more sensors located in the vehicle including i) one or more cameras, and ii) a motion sensing device, to monitor the driver of the vehicle.

In step 808, evaluating drowsiness of the driver based on observed body language and facial analysis of the driver, to detect and classify two or more levels of drowsiness of the driver of the vehicle.

In step 810, in an embodiment, integrating a multi-modal analysis from i) the sensors and the models that indicate drowsiness the driver, where the driver drowsiness module integrates the multi-modal analysis on two or more features including: i) facial expression analysis, ii) driver's gaze behavior analysis, iii) eye blinking profiles and analysis, and iv) eye closure pattern analysis, and in an embodiment, the analysis includes all four features.

In step 812, analyzing live multi-modal sensor inputs from the sensors against at least one of i) a trained machine-learning model and ii) a rules based model or iii) both while the driver is driving the vehicle to produce an output comprising a driver drowsiness-level estimation, where the driver drowsiness module using the trained machine-learning model and/or the rules based model is configured to utilize fewer computing cycles to classify a current level of drowsiness of the driver of the vehicle than the driver drowsiness module not using the trained machine-learning model and/or the rules based model.

In step 814, using both i) a generic drowsy-level machine learning model trained on analyzing the two or more features of the driver to recognize the two or more levels of drowsiness of the driver of the vehicle as well as ii) a user-personalized drowsy-level machine-learning model trained on any specifics of this driver to recognize the two or more levels of drowsiness of the driver, where the combination of the generic drowsy-level machine learning model trained on analyzing the two or more features of the driver and the user-personalized drowsy-level machine-learning model trained on any specifics of this driver causes the evaluation engine to more rapidly recognize the level of drowsiness of the driver than by using the generic drowsy-level machine learning model by itself.

In step 816, using a driver assistance module to attempt to maintain the driver i) in a non-drowsiness level, ii) at or below a first level of drowsiness of the driver, and iii) any combination of both, based on an output from the driver drowsiness module; and, when the driver is not at least at or below the first level of drowsiness of the driver, then the driver assistance module is configured to provide one or more positive assistance mechanisms back to the driver to attempt to change the driver's level to the level of i) where the driver is the non-drowsiness level, ii) where the driver's level of drowsiness is lowered to a lower level of drowsiness, and iii) any combination of both.

In step 818, using a driver assistance module to provide a positive assistance mechanism of engaging the driver with a personalized spoken summary through speakers of the vehicle, based on the driver's current level of drowsiness as determined by the driver drowsiness module, that is i) variable in decibel level, ii) selection of what kind of content of a document that the driver assistance module believes to be of interest to the driver, or iii) both variable in decibel level as well as what kind of content of the document that the system believes to be of interest to the driver.

Figure 9:
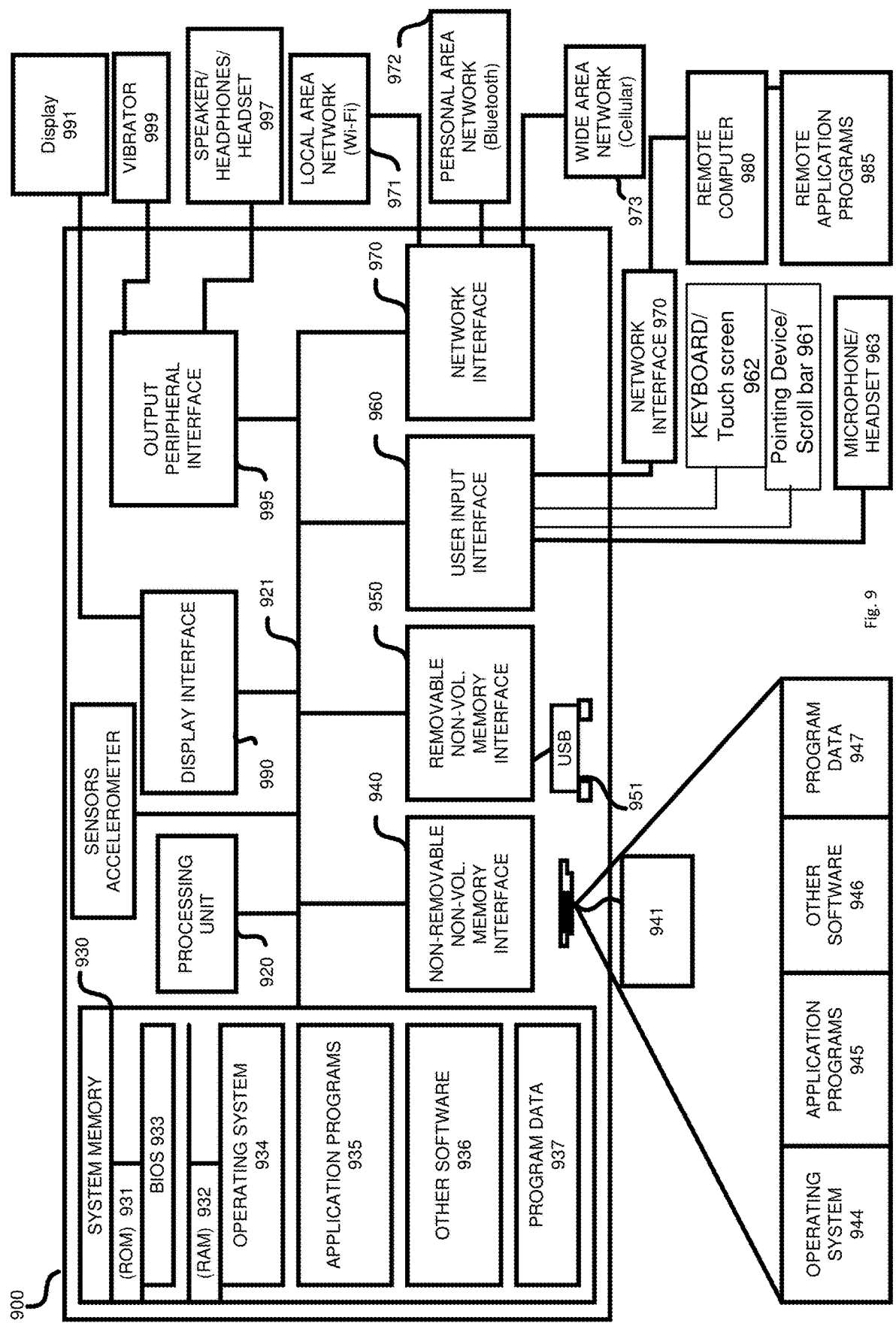
FIG. 9 illustrates an embodiment of one or more computing devices that can be a part of the evaluation engine.

FIG. 9 illustrates an embodiment of one or more computing devices 900 that can be a part of the evaluation engine. The computing device may include one or more processors or processing units 920 to execute instructions, one or more memories 930-932 to store information, one or more data input components 960-963 to receive data input from a user of the computing device 900, one or more modules that include the management module, a network interface communication circuit 970 to establish a communication link to communicate with other computing devices external to the computing device, one or more sensors where an output from the sensors is used for sensing a specific triggering condition and then correspondingly generating one or more preprogrammed actions, a display screen 991 to display at least some of the information stored in the one or more memories 930-932 and other components. Note, portions of the evaluation engine system implemented in software 944, 945, 946 are stored in the one or more memories 930-932 and are executed by the one or more processors 920.

Components of the computing system 900 may include, but are not limited to, a processing unit 920 having one or more processing cores, a system memory 930, and a system bus 921 that couples various system components including the system memory 930 to the processing unit 920. The system bus 921 may be any of several types of bus structures selected from a memory bus, an interconnect fabric, a peripheral bus, and a local bus using any of a variety of bus architectures.

Computing system 900 typically includes a variety of computing machine-readable media. Computing machine-readable media can be any available media that can be accessed by computing system 900 and includes both volatile and nonvolatile media, and removable and non-removable media. By way of example, and not limitation, computing machine-readable media use includes storage of information, such as computer-readable instructions, data structures, other executable software, or other data. Computer-storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other tangible medium which can be used to store the desired information and which can be accessed by the computing device 900. Transitory media, such as wireless channels, are not included in the machine-readable media. Communication media typically embody computer readable instructions, data structures, other executable software, or other transport mechanism and includes any information delivery media.

The system memory 930 includes computer storage media in the form of volatile and/or nonvolatile memory such as read only memory (ROM) 931 and random access memory (RAM) 932. A basic input/output system 933 (BIOS) containing the basic routines that help to transfer information between elements within the computing system 900, such as during start-up, is typically stored in ROM 931. RAM 932 typically contains data and/or software that are immediately accessible to and/or presently being operated on by the processing unit 920. By way of example, and not limitation, the RAM 932 can include a portion of the operating system 934, application programs 935, other executable software 936, and program data 937.

The computing system 900 can also include other removable/non-removable volatile/nonvolatile computer storage media. By way of example only, FIG. 9 illustrates a solid-state memory 941. Other removable/non-removable, volatile/nonvolatile computer storage media that can be used in the example operating environment include, but are not limited to, USB drives and devices, flash memory cards, solid state RAM, solid state ROM, and the like. The solid-state memory 941 is typically connected to the system bus 921 through a non-removable memory interface such as interface 940, and USB drive 951 is typically connected to the system bus 921 by a removable memory interface, such as interface 950.

The drives and their associated computer storage media discussed above and illustrated in FIG. 9, provide storage of computer readable instructions, data structures, other executable software, and other data for the computing system 900. In FIG. 9, for example, the solid-state memory 941 is illustrated for storing operating system 944, application programs 945, other executable software 946, and program data 947. Note that these components can either be the same as or different from operating system 934, application programs 935, other executable software 936, and program data 937. Operating system 944, application programs 945, other executable software 946, and program data 947 are given different numbers here to illustrate that, at a minimum, they are different copies.

A user may enter commands and information into the computing system 900 through input devices such as a keyboard, touchscreen, or software or hardware input buttons 962, a microphone 963, a pointing device and/or scrolling input component, such as a mouse, trackball or touch pad. The microphone 963 can cooperate with speech recognition software. These and other input devices are often connected to the processing unit 920 through a user input interface 960 that is coupled to the system bus 921, but can be connected by other interface and bus structures, such as a parallel port, game port, or a universal serial bus (USB). A display monitor 991 or other type of display screen device is also connected to the system bus 921 via an interface, such as a display interface 990. In addition to the monitor 991, computing devices may also include other peripheral output devices such as speakers 997, a vibrator 999, and other output devices, which may be connected through an output peripheral interface 995.

The computing system 900 can operate in a networked environment using logical connections to one or more remote computers/client devices, such as a remote computing system 980. The remote computing system 980 can a personal computer, a mobile computing device, a server, a router, a network PC, a peer device or other common network node, and typically includes many or all of the elements described above relative to the computing system 900. The logical connections depicted in FIG. 9 can include a personal area network (PAN) 972 (e.g., Bluetooth®), a local area network (LAN) 971 (e.g., Wi-Fi), and a wide area network (WAN) 973 (e.g., cellular network), but may also include other networks such as a personal area network (e.g., Bluetooth®). Such networking environments are commonplace in offices, enterprise-wide computer networks, intranets and the Internet. A browser application may be resident on the computing device and stored in the memory.

When used in a LAN networking environment, the computing system 900 is connected to the LAN 971 through a network interface 970, which can be, for example, a Bluetooth® or Wi-Fi adapter. When used in a WAN networking environment (e.g., Internet), the computing system 900 typically includes some means for establishing communications over the WAN 973. With respect to mobile telecommunication technologies, for example, a radio interface, which can be internal or external, can be connected to the system bus 921 via the network interface 970, or other appropriate mechanism. In a networked environment, other software depicted relative to the computing system 900, or portions thereof, may be stored in the remote memory storage device. By way of example, and not limitation, FIG. 9 illustrates remote application programs 985 as residing on remote computing device 980. It will be appreciated that the network connections shown are examples and other means of establishing a communications link between the computing devices that may be used.

As discussed, the computing system 900 can include a processing unit 920, a memory (e.g., ROM 931, RAM 932, etc.), a built in battery to power the computing device, an AC power input to charge the battery, a display screen, a built-in Wi-Fi circuitry to wirelessly communicate with a remote computing device connected to network.

It should be noted that the present design can be carried out on a computing system such as that described with respect to FIG. 9. However, the present design can be carried out on a server, a computing device devoted to message handling, or on a distributed system in which different portions of the present design are carried out on different parts of the distributed computing system.

Another device that may be coupled to bus 921 is a power supply such as a DC power supply (e.g., battery) or an AC adapter circuit. As discussed above, the DC power supply may be a battery, a fuel cell, or similar DC power source that needs to be recharged on a periodic basis. A wireless communication module can employ a Wireless Application Protocol to establish a wireless communication channel. The wireless communication module can implement a wireless networking standard.

In some embodiments, software used to facilitate algorithms discussed herein can be embodied onto a non-transitory machine-readable medium. A machine-readable medium includes any mechanism that stores information in a form readable by a machine (e.g., a computer). For example, a non-transitory machine-readable medium can include read only memory (ROM); random access memory (RAM); magnetic disk storage media; optical storage media; flash memory devices; Digital Versatile Disc (DVD's), EPROMs, EEPROMs, FLASH memory, magnetic or optical cards, or any type of media suitable for storing electronic instructions.

Note, algorithms herein may be implemented in software by itself, hardware Boolean logic by itself, or some combination of both. Any portions of an algorithm implemented in software can be stored in an executable format in portion of a memory and is executed by one or more processors.

Note, an application described herein includes but is not limited to software applications, mobile applications, and programs that are part of an operating system application. Some portions of this description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. These algorithms can be written in a number of different software programming languages such as C, C+, HTTP, Java, or other similar languages. Also, an algorithm can be implemented with lines of code in software, configured logic gates in software, or a combination of both. In an embodiment, the logic consists of electronic circuits that follow the rules of Boolean Logic, software that contain patterns of instructions, or any combination of both.

It should be borne in mind, however, that all of these and similar terms are to be associated with the appropriate physical quantities and are merely convenient labels applied to these quantities. Unless specifically stated otherwise as apparent from the above discussions, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers, or other such information storage, transmission or display devices.

Many functions performed by electronic hardware components can be duplicated by software emulation. Thus, a software program written to accomplish those same functions can emulate the functionality of the hardware components in input-output circuitry. Thus, provided herein are one or more non-transitory machine-readable medium configured to store instructions and data that when executed by one or more processors on the computing device of the foregoing system, causes the computing device to perform the operations outlined as described herein.

While the foregoing design and embodiments thereof have been provided in considerable detail, it is not the intention of the applicant(s) for the design and embodiments provided herein to be limiting. Additional adaptations and/or modifications are possible, and, in broader aspects, these adaptations and/or modifications are also encompassed. Accordingly, departures may be made from the foregoing design and embodiments without departing from the scope afforded by the following claims, which scope is only limited by the claims when appropriately construed.

What is claimed is:

1. An evaluation engine having two or more modules to monitor a driver of a vehicle, comprising:
    a driver drowsiness module that is configured to analyze monitored features of the driver to be capable to recognize two or more levels of drowsiness of the driver of the vehicle;
    a facial analysis module that is configured to be capable to perform at least two of i) face tracking, ii) eye movement and iii) eye blink tracking on the driver of the vehicle to assist in detecting the levels of drowsiness of the driver of the vehicle, where an output analysis of the facial analysis module is supplied to the driver drowsiness module;
    a sensor interface that is located among the two or more modules, including the facial analysis module and the driver drowsiness module, and one or more sensors, where the sensor interface is configured to receive input from the one or more sensors located in the vehicle including i) one or more cameras, and ii) a motion sensing device coupled with a speech user interface, to monitor the driver of the vehicle;
    where the driver drowsiness module is configured to utilize the output of the facial analysis module to evaluate drowsiness of the driver based on at least one of observed body language and facial analysis of the driver, to detect and classify one or more levels of drowsiness of the driver of the vehicle when those states occur for the driver;
    a driver assistance module that is configured to attempt to maintain the driver in a level selected from a group consisting of i) in a non-drowsiness level, ii) at or below a first level of drowsiness of the driver, and iii) any combination of both, based on an output from the driver drowsiness module; and, when the driver is not at least at or below the first level of drowsiness of the driver, then the driver assistance module is configured to provide one or more positive assistance mechanisms back to the driver to attempt to change the driver's level to the level of i) where the driver is the non-drowsiness level, ii) where the driver's level of drowsiness is lowered to a lower level of drowsiness, and iii) any combination of both, where the evaluation engine with its two or more modules is adaptive on providing a level of assistance that the driver needs in order to get back to any of i) the non-drowsiness level, and/or ii) one of the levels of drowsiness of the driver, based on feedback collected from the driver from the sensor interface, and an assessment by the driver assistance module of what effect a first level of assistance provided to the driver had on a current level of drowsiness of the driver.

2. The evaluation engine of claim 1, where the driver assistance module is configured to monitor what effect the first level of assistance provided to the driver had on the level of drowsiness of the driver and determine whether additional or combinations of different types of assistance should further be presented to the driver to return the driver to at least a desired level of drowsiness.

3. The evaluation engine of claim 2, where the driver assistance module is configured to provide one or more additional or combinations of different types of assistance back to the driver to attempt to change the driver's level of drowsiness including running a fan, running an air conditioner, changing a temperature in the car of the driver, shaking a seat of the driver, and changing a smell in a vehicle of the driver.

4. The evaluation engine of claim 1, where one or more driver-drowsiness machine-learning models utilize ground truth correlations and deep learning machine learning algorithms to train the models, and where the one or more driver-drowsiness machine-learning models use a drowsiness level classification scheme that has at least three or more different levels of drowsiness of the driver, and
    once the one or more driver-drowsiness machine-learning models are trained, they are used to analyze live multi-modal sensor inputs from the sensors while the driver is operating the vehicle to produce an output including a current level of drowsiness estimation specific to that driver.

5. The evaluation engine of claim 1, where the sensor interface is configured to receive a multi-modal sensor input from at least three sensors including i) the motion sensing device coupled with the speech user interface that includes a microphone, ii) a hi-resolution InfraRed camera that is coupled to one or more InfraRed light sources in the vehicle that are positioned to narrowly focus on a face of the driver, and iii) a wide-angle lens camera positioned to capture a view of the driver's head and upper body.

6. The evaluation engine of claim 1, where the facial analysis module has an ocular activity analysis module that is configured to cooperate with an infra-red light source to track a direction of a head of the driver relative a steering wheel of the vehicle and an angle of a gaze of the eyes of the driver of the vehicle, where the ocular activity analysis module implements a glint-based tracking mechanism that tracks corneal glints from the infra-red light source.

7. The evaluation engine of claim 1, where the driver drowsiness module is configured to detect and classify three or more levels of drowsiness of the driver of the vehicle, including at least marginally drowsy, moderately drowsy, and significantly drowsy, when those states occur for the driver; and where the evaluation engine with its two or more modules is configured to adapt an interactive conversation between itself and the driver in real time, based on the feedback from the driver and a current level of drowsiness of the driver from the three of more levels of drowsiness as indicated by an output from the driver activity tracking module.

8. The evaluation engine of claim 1, where the driver assistance module is configured to provide a first positive assistance mechanism of engaging the driver with a personalized spoken summary as the first level of assistance, based on the driver's current level of drowsiness from the three of more levels of drowsiness, as determined by the driver drowsiness module, that is i) variable in decibel level, ii) selection of what kind of content of a document that the driver assistance module believes to be of interest to the driver, or iii) both variable in decibel level as well as what kind of content of the document that the system believes to be of interest to the driver.

9. The evaluation engine of claim 8, where the driver assistance module utilizes a document summarization engine to produce an extractive summary of the content of the document, where a driver-specific preference model extracts driver preferences from texts, browsing habits, and input solicited from the user, where a text-to-speech subsystem that works with the driver assistance module is used to prepare the summarized content of the document to report to the driver through a speaker of the vehicle.

10. The evaluation engine of claim 8, where the driver assistance module is further configured to monitor and evaluate i) the level of drowsiness of the driver as the personalized spoken summary is occurring and ii) what kind of content of the document is being presented as the level of drowsiness of the driver changes.

11. The evaluation engine of claim 1, where a driver activity analysis module is configured to cooperate with the sensor interface to use a camera in the motion sensing device to track a driver's upper-body, where the driver activity analysis module is configured to track the driver's upper-body posture and movement using the motion sensor's data stream.

12. A method for an evaluation engine monitoring a driver of a vehicle, comprising:

analyzing monitored features of the driver to recognize one or more levels of drowsiness of the driver of the vehicle with a driver drowsiness module, using one or more sensors located in the vehicle including i) one or more cameras, and ii) a motion sensing device, to monitor the driver of the vehicle, tracking the face of the driver and performing at least one of i) face tracking, ii) eye movement and iii) eye blink tracking on the driver of the vehicle to assist in detecting the levels of drowsiness of the driver of the vehicle, and supplying this output to a driver drowsiness module, evaluating drowsiness of the driver based on observed body language and facial analysis of the driver, to detect and classify the one or more levels of drowsiness of the driver of the vehicle, adaptively providing a level of assistance that the driver needs in order to get back to any of i) a non-drowsiness level, and/or ii) one of the levels of drowsiness of the driver, based on feedback collected from the driver and an assessment of what effect a first level of assistance provided to the driver had on a current level of drowsiness of the driver, and analyzing live multi-modal sensor inputs from the sensors against at least one of i) a trained machine-learning model and ii) a rules based model or iii) both while the vehicle is started to produce an output comprising a driver drowsiness-level estimation, where the driver drowsiness module using the trained machine-learning model and/or the rules based model is configured to utilize fewer computing cycles to classify a current level of drowsiness of the driver of the vehicle than the driver drowsiness module not using the trained machine-learning model and/or the rules based model.

13. The method of claim 12, further comprising:
using a driver assistance module to attempt to maintain the driver in a level selected from a group consisting of i) in the non-drowsiness level, ii) at or below a first level of drowsiness of the driver, and iii) any combination of both, based on an output from the driver drowsiness module and when the driver is not at least at or below the first level of drowsiness of the driver, then the driver assistance module is configured to provide one or more additional or combinations of different types of assistance back to the driver to attempt to change the driver's level of drowsiness including running a fan, running an air conditioner, changing a temperature in the car of the driver, shaking a seat of the driver, and changing a smell in a vehicle of the driver.

14. The method of claim 12, further comprising:
using both i) a generic drowsy-level machine learning model trained on analyzing the tracked features of the face of the driver to recognize the two or more levels of drowsiness of the driver of the vehicle as well as ii) a user-personalized drowsy-level machine-learning model trained on any specifics of this driver to recognize the one or more levels of drowsiness of the driver, where the combination of the generic drowsy-level machine learning model trained on analyzing the two or more features of the driver and the user-personalized drowsy-level machine-learning model trained on any specifics of this driver causes the evaluation engine to more rapidly recognize the level of drowsiness of the driver than by using the generic drowsy-level machine learning model by itself.

15. The method of claim 12, further comprising:
using a driver assistance module to provide a first positive assistance mechanism of engaging the driver with a personalized spoken summary through speakers of the vehicle, based on the driver's current level of drowsiness from three of more levels of drowsiness as determined by the driver drowsiness module, that is i) variable in decibel level, ii) selection of what kind of content of a document that the driver assistance module believes to be of interest to the driver, or iii) both variable in decibel level as well as what kind of content of the document that the system believes to be of interest to the driver, where the driver drowsiness module is configured to detect and classify three or more levels of drowsiness of the driver of the vehicle, including at least marginally drowsy, moderately drowsy, and significantly drowsy, when those states occur for the driver; and monitoring what effect the first positive assistance mechanism of engaging the driver provided to the driver had on the level of drowsiness of the driver and determine whether additional or combinations of different types of assistance should further be presented to the driver to return the driver to at least a desired level of drowsiness.

16. The method of claim 12, further comprising:

integrating a multi-modal analysis from i) the sensors and the models that indicates a drowsiness level of the driver, where the driver drowsiness module integrates the multi-modal analysis on two or more features including: i) facial expression analysis for the face tracking, ii) driver's gaze behavior analysis for the eye movement, iii) eye blinking profiles and analysis for the eye blink tracking, and iv) eye closure pattern analysis.

17. An evaluation engine having two or more modules monitoring a driver of a vehicle, comprising:

a driver drowsiness module that is configured to analyze monitored features of the driver to recognize one or more levels of drowsiness of the driver of the vehicle, a facial analysis module that is configured to perform at least one of i) face tracking, ii) eye movement and iii) eye blink tracking on the driver of the vehicle to assist in detecting the levels of drowsiness of the driver of the vehicle, where an output analysis of the facial analysis module is supplied to the driver drowsiness module, a sensor interface is located among the two or more modules, including the facial analysis module and the driver drowsiness module, and one or more sensors located in the vehicle including i) one or more cameras, and ii) a motion sensing device, to monitor the driver of the vehicle, and where the driver drowsiness module is configured to utilize the output of the facial analysis module to evaluate drowsiness of the driver based on observed body language and facial analysis of the driver, to detect and classify the one or more levels of drowsiness of the driver of the vehicle, where the driver drowsiness module is configured to analyze live multi-modal sensor inputs from the sensors against at least one of i) a trained machine-learning model, ii) a rules, or iii) both based model while the driver is driving the vehicle to produce an output comprising a driver drowsiness-level estimation, where the driver drowsiness module using the trained machine-learning model and/or the rules based model is configured to utilize fewer computing cycles to classify a current level of drowsiness of the driver of the vehicle than the driver drowsiness module not using the trained machine-learning model and/or the rules based model, where the evaluation engine with its two or more modules is configured to be adaptive on providing a level of assistance that the driver needs in order to get back to any of i) a non-drowsiness level, and/or ii) one of the three or more levels of drowsiness of the driver, based on feedback collected from the driver from the sensor interface, and an assessment by the driver assistance module of what effect a first level of assistance provided to the driver had on a current level of drowsiness of the driver.

18. The evaluation engine of claim 17, further comprising:

a driver assistance module that is configured to attempt to maintain the driver in a level selected from a group consisting of i) in a non-drowsiness level, ii) at or below a first level of drowsiness of the driver, and iii) any combination of both, based on an output from the driver drowsiness module; and, when the driver is not at least at or below the first level of drowsiness of the driver, then the driver assistance module is configured to provide one or more positive assistance mechanisms back to the driver to attempt to change the driver's level to the level of i) where the driver is the non-drowsiness level, ii) where the driver's level of drowsiness is lowered to a lower level of drowsiness, and iii) any combination of both, and where the driver assistance module is configured to monitor what effect the first level of assistance provided to the driver had on the current level of drowsiness of the driver and determine whether additional or combinations of different types of assistance should further be presented to the driver to return the driver to at least a desired level of drowsiness.

19. The evaluation engine of claim 17, where the machine-learning model trained on detecting drowsiness indicators of the driver includes both i) a generic drowsy-level machine learning model trained on analyzing the two or more features of the driver to recognize three or more levels of drowsiness of the driver of the vehicle, including at least marginally drowsy, moderately drowsy, and significantly drowsy, as well as ii) a user-personalized drowsy-level machine-learning model trained on any specifics of this driver to recognize the three or more levels of drowsiness of the driver, and where the evaluation engine with its two or more modules is configured to adapt an interactive conversation between itself and the driver in real time based on the feedback from the driver and the current level of drowsiness of the driver as indicated by an output from the driver activity tracking module.

20. The evaluation engine of claim 18, where the driver assistance module is configured to provide a first positive assistance mechanism of engaging the driver with a personalized spoken summary through speakers of the vehicle, based on the driver's current level of drowsiness as determined by the driver drowsiness module, that is i) variable in decibel level, ii) selection of what kind of content of a document that the driver assistance module believes to be of interest to the driver, or iii) both variable in decibel level as well as what kind of content of the document that the system believes to be of interest to the driver.

* * * * *